United States Patent
Zheng

(10) Patent No.: US 11,801,096 B2
(45) Date of Patent: Oct. 31, 2023

(54) APPARATUS AND METHOD FOR TRACKING A MEDICAL ULTRASONIC OBJECT

(71) Applicant: C. R. Bard, Inc., Franklin Lakes, NJ (US)

(72) Inventor: Peng Zheng, Chandler, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 94 days.

(21) Appl. No.: 16/649,902

(22) PCT Filed: Sep. 29, 2017

(86) PCT No.: PCT/US2017/054251
§ 371 (c)(1),
(2) Date: Mar. 23, 2020

(87) PCT Pub. No.: WO2019/066888
PCT Pub. Date: Apr. 4, 2019

(65) Prior Publication Data
US 2020/0268455 A1 Aug. 27, 2020

(51) Int. Cl.
*A61B 34/20* (2016.01)
*A61B 8/08* (2006.01)
(Continued)

(52) U.S. Cl.
CPC ............ *A61B 34/20* (2016.02); *A61B 8/0841* (2013.01); *A61B 8/461* (2013.01); *A61B 8/488* (2013.01);
(Continued)

(58) Field of Classification Search
CPC .......... A61B 17/22012; A61B 17/3207; A61B 2017/00137; A61B 2017/22014;
(Continued)

(56) References Cited

U.S. PATENT DOCUMENTS

| 6,233,476 B1 | 5/2001 | Strommer et al. |
| 7,396,332 B2 | 7/2008 | Taimisto et al. |

(Continued)

FOREIGN PATENT DOCUMENTS

| CN | 106999146 B | 11/2020 |
| KR | 2015-0118495 A | 10/2015 |
| WO | 2014189966 A1 | 11/2014 |

OTHER PUBLICATIONS

Office Action dated Mar. 29, 2022, pertaining to Korean application 10-2020-7010852.

(Continued)

*Primary Examiner* — Joseph M Santos Rodriguez
*Assistant Examiner* — Maria Christina Talty
(74) *Attorney, Agent, or Firm* — Dinsmore & Shohl LLP

(57) ABSTRACT

A vascular occlusion treatment system includes an ultrasound imaging system having an imaging control circuit communicatively coupled to an ultrasound imaging probe and to a display screen, and an ultrasonic vibration system having an ultrasonic generator operatively coupled to a medical ultrasonic object, such as an ultrasonic catheter. The ultrasonic catheter has a corewire with a distal tip. The ultrasonic generator has a generator control circuit that alternatingly switches between an ultrasonic work frequency and a tracking frequency. The generator control circuit sends a notification to the imaging control circuit when the generator control circuit has switched from the ultrasonic work frequency to the tracking frequency. The imaging control circuit responds by initiating a search in an ultrasound imaging space to locate the distal tip that is vibrating at the tracking frequency, and indicating a location of the distal tip in the ultrasound image displayed on the display screen.

20 Claims, 3 Drawing Sheets

(51) Int. Cl.
*A61B 8/00* (2006.01)
*A61B 17/22* (2006.01)
*A61B 90/00* (2016.01)
*A61B 17/00* (2006.01)

(52) U.S. Cl.
CPC .............. *A61B 17/22012* (2013.01); *A61B 2017/00137* (2013.01); *A61B 2017/22014* (2013.01); *A61B 2034/2063* (2016.02); *A61B 2034/2065* (2016.02); *A61B 2090/378* (2016.02)

(58) Field of Classification Search
CPC .. A61B 2017/22094; A61B 2017/3413; A61B 2034/2063; A61B 2034/2065; A61B 2090/378; A61B 2090/3782; A61B 2090/3929; A61B 34/20; A61B 8/0833; A61B 8/0841; A61B 8/461; A61B 8/488; A61B 8/5223; A61M 2025/0166; B06B 1/0607; G16H 50/30
See application file for complete search history.

(56) References Cited

U.S. PATENT DOCUMENTS

| | | | |
|---|---|---|---|
| 7,713,210 B2 | 5/2010 | Byrd et al. | |
| 8,038,621 B2* | 10/2011 | Baba | A61B 8/0833 600/459 |
| 8,200,313 B1 | 6/2012 | Rambod et al. | |
| 8,403,858 B2 | 3/2013 | Abraham | |
| 8,403,859 B2 | 3/2013 | Abraham | |
| 8,690,819 B2 | 4/2014 | Nita et al. | |
| 8,876,723 B2 | 11/2014 | Hauck | |
| 8,932,226 B2 | 1/2015 | Hossack et al. | |
| 9,113,826 B2 | 8/2015 | Osumi | |
| 9,121,926 B2 | 9/2015 | Nair et al. | |
| 9,149,257 B2 | 10/2015 | Abraham | |
| 9,282,946 B2 | 3/2016 | Vignon et al. | |
| 2008/0139971 A1* | 6/2008 | Lockhart | A61N 7/00 601/2 |
| 2008/0294037 A1* | 11/2008 | Richter | A61B 17/2202 600/424 |
| 2009/0182224 A1 | 7/2009 | Shmarak et al. | |
| 2009/0292204 A1* | 11/2009 | Pansky | A61B 8/488 600/439 |
| 2010/0305432 A1* | 12/2010 | Duhay | A61B 8/483 600/424 |
| 2011/0160588 A1 | 6/2011 | Ichikawa | |
| 2012/0095461 A1* | 4/2012 | Herscher | A61B 18/1206 606/45 |
| 2012/0283565 A1 | 11/2012 | Richter | |
| 2015/0366536 A1 | 12/2015 | Courtney et al. | |
| 2016/0007947 A1 | 1/2016 | Spencer et al. | |
| 2016/0331399 A1* | 11/2016 | Tsubuku | H01L 41/042 |

OTHER PUBLICATIONS

Office Action dated May 5, 2023 pertaining to CN application 201780096410.2.

* cited by examiner

APPARATUS AND METHOD FOR TRACKING A MEDICAL ULTRASONIC OBJECT

CROSS-REFERENCE TO RELATED APPLICATIONS

This application is a U.S. national phase of International Application No. PCT/US2017/054251, filed Sep. 29, 2017, which is incorporated herein by reference in its entirety and from which priority is claimed.

TECHNICAL FIELD

The present invention relates to tracking a medical object in a patient, and, more particularly, to an apparatus and method for tracking a medical ultrasonic object in a patient, such as in a vascular occlusion treatment system.

BACKGROUND ART

An ultrasonic catheter system is disclosed in U.S. Pat. No. 8,690,819, in which an ultrasound-activated catheter (hereinafter, ultrasonic catheter) is used to conduct atherectomy and disruption of blood vessel obstructions, such as vascular occlusions, by ablating the calcified plaque in a blood vessel of a vasculature. The ultrasonic catheter system includes an ultrasound vibration source configured to generate a vibration motion, which is coupled to a portion of the ultrasonic catheter.

In particular, the ultrasonic catheter has a catheter sheath having a lumen, and has an ultrasound transmission member that is movably disposed within the lumen of the catheter sheath. The ultrasound transmission member has a proximal portion that is coupled to the ultrasound vibration source via an ultrasound transducer, which transfers vibration motion to the ultrasound transmission member. A distal portion of the ultrasound transmission member may be exposed from the catheter sheath. In operation, the distal portion is excited by an ultrasound wave generated by the ultrasound transducer, resulting in longitudinal and transverse mechanical vibration at the distal portion of the ultrasound transmission member of the ultrasonic catheter, which in turn ablates the calcified lesion in the blood vessel of the vasculature.

What is needed in the art is an apparatus and method that utilizes an ultrasound imaging system to locate, track, and display the location of a medical ultrasonic object, such as an ultrasonic catheter, during a medical procedure.

SUMMARY OF INVENTION

The present invention provides an apparatus and method that utilizes ultrasound imaging to locate and track a medical ultrasonic object in a patient during a medical procedure, and to display the location of the medical ultrasonic object on a display screen of the ultrasound imaging system.

The invention, in one form, is directed to a vascular occlusion treatment system that includes an ultrasound imaging system and an ultrasonic vibration system. The ultrasound imaging system has an imaging control circuit communicatively coupled to each of an ultrasound imaging probe and a display screen. The ultrasound imaging system is configured to generate an ultrasound image for display on the display screen from ultrasound imaging data collected from an ultrasound imaging space. The ultrasound vibration system has an ultrasonic generator operatively coupled to an ultrasonic catheter. The ultrasonic catheter has a corewire with a distal tip. The ultrasonic generator has a generator control circuit configured to alternatingly switch between an ultrasonic work frequency and a tracking frequency. The generator control circuit is communicatively coupled to the imaging control circuit. The generator control circuit is configured to execute program instructions to send a notification to the imaging control circuit when the generator control circuit has switched from the ultrasonic work frequency to the tracking frequency. The imaging control circuit is configured to respond to the notification by executing program instructions to: initiate a search in the ultrasound imaging space to locate the distal tip of the corewire of the ultrasonic catheter that is vibrating at the tracking frequency, and indicate a location of the distal tip in the ultrasound image displayed on the display screen.

The invention, in another form, is directed to a method for tracking a medical ultrasonic object using an ultrasound imaging system having an ultrasound imaging probe and a display screen, the ultrasound imaging probe generating ultrasound imaging data in an ultrasound imaging space for generation of an ultrasound image for display on the display screen. The method includes alternatingly vibrating the medical ultrasonic object at an ultrasonic work frequency and at a tracking frequency, the ultrasonic work frequency and the tracking frequency being different frequencies; notifying the ultrasound imaging system of a change from the ultrasonic work frequency to the tracking frequency; initiating a search by the ultrasound imaging system to search in the ultrasound imaging space to locate the medical ultrasonic object that is vibrating at the tracking frequency; and indicating a location of the medical ultrasonic object in the ultrasound image displayed on the display screen.

The invention, in another form, is directed to a method of locating a distal tip of an ultrasonic catheter used in conjunction with an ultrasound imaging system having an ultrasound imaging probe and a display screen, the ultrasound imaging probe generating ultrasound imaging data in an ultrasound imaging space for generation of an ultrasound image for display on the display screen. The method includes establishing an ultrasonic work frequency for the distal tip of the corewire of the ultrasonic catheter; establishing a tracking frequency for the distal tip of the corewire of the ultrasonic catheter that is different from the ultrasonic work frequency; alternating an operation of the ultrasonic catheter between vibrating the distal tip at the ultrasonic work frequency and vibrating the distal tip at the tracking frequency; notifying the ultrasound imaging system of the change in operation of the ultrasonic catheter from the ultrasonic work frequency to the tracking frequency; in response to the notifying, initiating a search by the ultrasound imaging system to locate in the ultrasound imaging space the distal tip of the corewire of the ultrasonic catheter that is vibrating at the tracking frequency; and indicating a location of the distal tip of the corewire of the ultrasonic catheter in the ultrasound image displayed on the display screen.

The invention, in another form, is directed to an alternative vascular occlusion treatment system, wherein the ultrasonic generator may have a generator control circuit configured to alternatingly switch between an output power level for treatment and an output power level for image tracking, while maintaining the same ultrasonic frequency. The generator output power level for treatment can transmit strong vibration energy into the catheter and cause the catheter distal portion, i.e., the active section, of the corewire to vibrate strongly at the ultrasonic frequency. The generator output power level for image tracking can transmit a relatively small energy into the ultrasonic catheter and cause the distal portion, i.e., the active section, of the corewire to vibrate, but not have any therapeutic effect. The generator control circuit is communicatively coupled to the imaging control circuit. The generator control circuit is configured to execute program instructions to send a notification to the imaging control circuit when the generator control circuit has switched from the treatment power level to the image tracking power level. The imaging control circuit is configured to respond to the notification by executing program instructions to initiate a search in the ultrasound imaging space utilizing a Doppler function. The Doppler function will only detect any moving components in the ultrasound imaging space. Therefore, the vibration of the distal portion, i.e., the active section, of the corewire of the ultrasonic catheter will be able to be detected by the ultrasound imaging system. After active averaging and filtering, the location of the distal tip of the corewire will be displayed in the ultrasound image displayed on the display screen of the ultrasound imaging system.

An advantage of the present invention is that the apparatus and method of the present invention do not require a separate tracking field generation system for generating a separate tracking field to be used in locating a medical object in a patient.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate an embodiment of the invention, and such exemplifications are not to be construed as limiting the scope of the invention in any manner.

DESCRIPTION OF EMBODIMENTS

Figure 1:
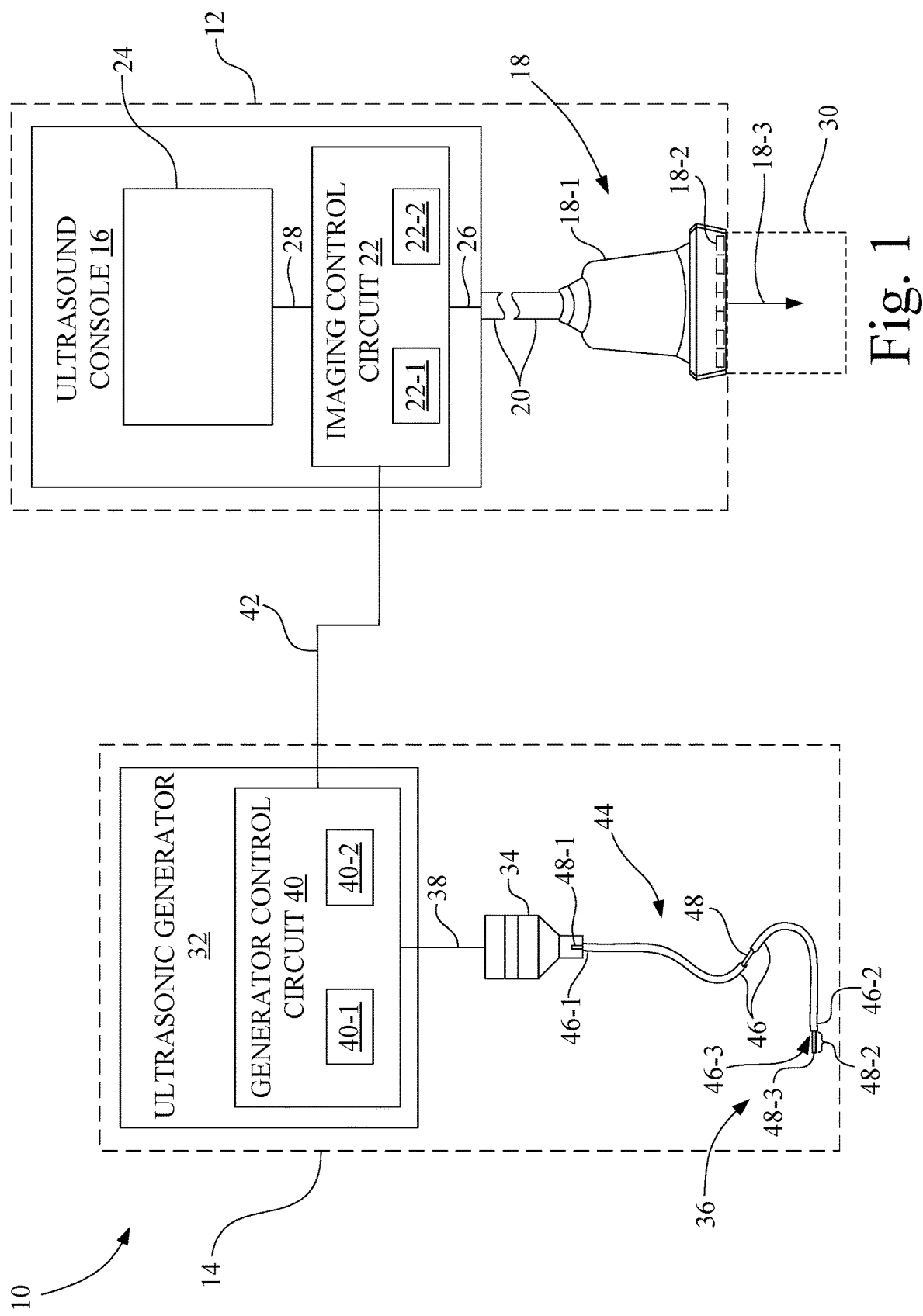
FIG. 1 is a circuit block diagram of a vascular occlusion treatment system that includes an ultrasound imaging system and an ultrasonic vibration system, which is configured to locate and track a medical ultrasonic object.

Referring now to the drawings, and more particularly to FIG. 1, there is shown a vascular occlusion treatment system 10 in accordance with an embodiment of the present invention. Vascular occlusion treatment system 10 includes an ultrasound imaging system 12 and an ultrasonic vibration system 14.

Figure 2:
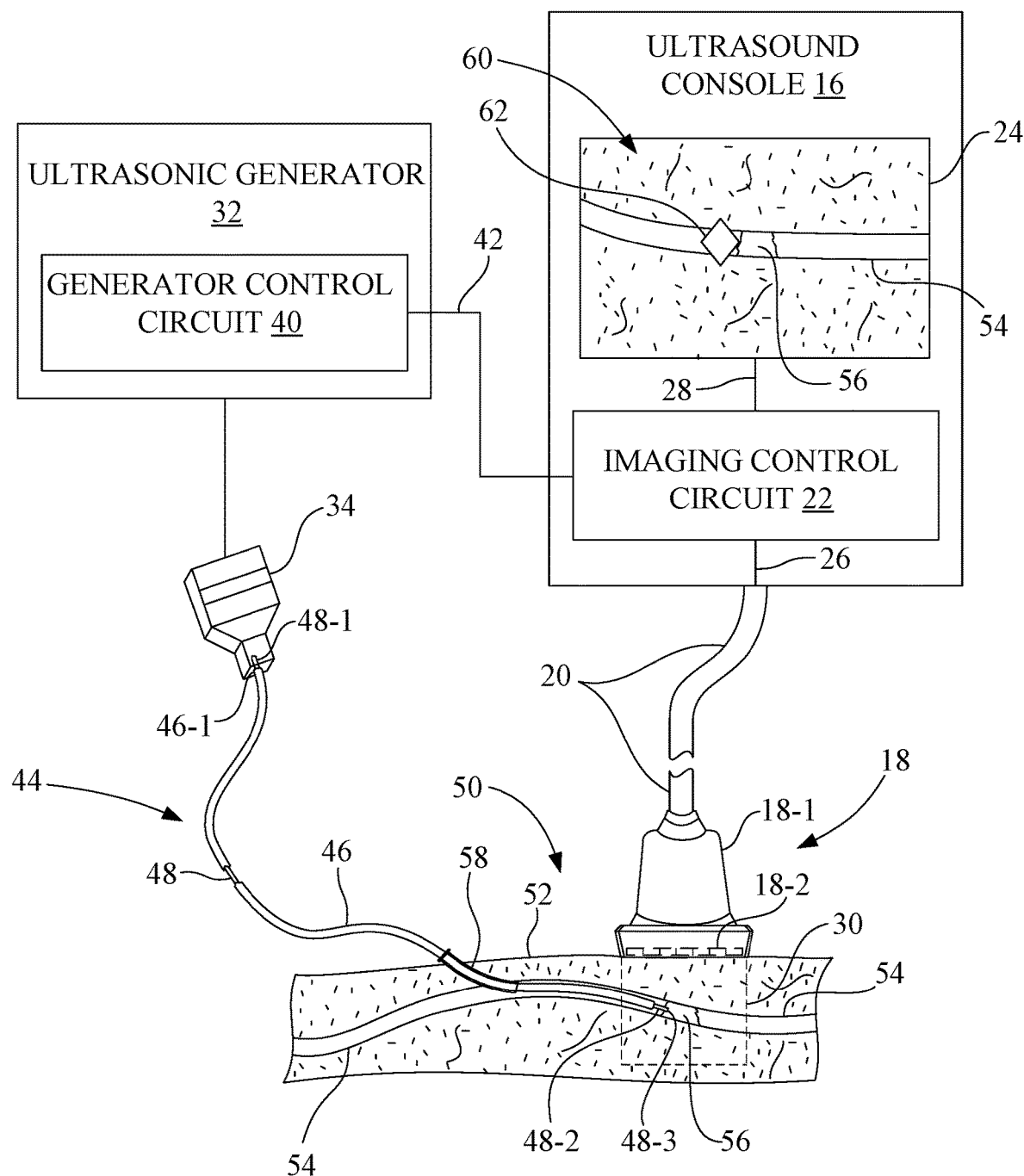
FIG. 2 is a graphical depiction of the use of the vascular occlusion treatment system of FIG. 1 during a vascular occlusion treatment procedure in locating and tracking the medical ultrasonic object.

Ultrasound imaging system 12 includes an ultrasound console 16 that is communicatively coupled to an ultrasound imaging probe 18, such as by a flexible communication cable 20, e.g., an electrical (multi-wire) cable. Ultrasound console 16 includes an imaging control circuit 22 and a display screen 24. Imaging control circuit 22 is communicatively coupled to each of ultrasound imaging probe 18 and display screen 24, e.g., by respective wired connections 26, 28. Referring also to FIG. 2, ultrasound imaging system 12 is configured to generate an ultrasound image 60 for display on display screen 24 from ultrasound imaging data collected from an ultrasound imaging space 30 defined by ultrasound imaging probe 18. In one embodiment, for example, ultrasound imaging space 30 may be represented by three-dimensional (3D) imaging data and the ultrasound image may be a two-dimensional (2D) ultrasound image or a 3D ultrasound image.

Ultrasound imaging probe 18 includes a probe housing 18-1 and an ultrasound transducer array 18-2. Ultrasound transducer array 18-2 may be configured as a transceiver that is communicatively coupled, e.g., via a wired connection, to imaging control circuit 22. Ultrasound transducer array 18-2 is mounted to, e.g., contained within, probe housing 18-1 and defines the ultrasound imaging space 30 as an ultrasound volume that extends along a Z-axis 18-3 from probe housing 18-1. Ultrasound transducer array 18-2 generates two-dimensional (2D) ultrasound slice data within the ultrasound field-of-view volume of ultrasound imaging space 30, wherein multiple sequential 2D ultrasound data slices may be merged, e.g., stitched together, to form a 3D dataset having 3D imaging data. In the present embodiment, for producing the 3D dataset, ultrasound transducer array 18-2 of ultrasound imaging probe 18 may be a two-dimensional (2D) matrix of piezoelectric elements that are electronically scanned in a sweeping motion. As such, the ultrasound imaging space 30 is comprised of a plurality of sequentially generated 2D ultrasound image slices. Alternatively, ultrasound transducer array 18-2 of ultrasound imaging probe 18 may be a mechanically movable one-dimensional (1D) linear array of piezoelectric elements that is mechanically scanned to generate a plurality of sequentially generated ultrasound image slices. As a further alternative, if desired, ultrasound transducer array 18-2 may be a fixed-position linear array (i.e., fixed with respect to probe housing 18-1) that generates a single ultrasound image slice (refreshed periodically), in which case the ultrasound imaging space 30 is narrowed to the thickness of the single ultrasound image slice.

In the present embodiment, imaging control circuit 22 is an electrical circuit that has data processing capability and command generating capability for processing imaging data generated by ultrasound imaging probe 18 and for generating an ultrasound image for display on display screen 24. In the present embodiment, imaging control circuit 22 has a microprocessor 22-1 and associated non-transitory electronic memory 22-2, as well as input/output (I/O) circuitry. Microprocessor 22-1 and associated non-transitory electronic memory 22-2 are commercially available components, as will be recognized by one skilled in the art. Microprocessor 22-1 may be in the form of a single microprocessor, or two or more parallel microprocessors, as is known in the art. Non-transitory electronic memory 22-2 may include multiple types of digital data memory, such as random access memory (RAM), non-volatile RAM (NVRAM), read only memory (ROM), and/or electrically erasable programmable read-only memory (EEPROM). Non-transitory electronic memory 22-2 may further include mass data storage in one or more of the electronic memory forms described above, or on a computer hard drive or optical disk. Alternatively, imaging control circuit 22 may be assembled as one or more Application Specific Integrated Circuits (ASIC).

Referring to FIGS. 1 and 2, ultrasound imaging space 30 may be represented by three-dimensional (3D) imaging data that is generated and stored in non-transitory electronic memory 22-2 of imaging control circuit 22. Imaging control circuit 22 processes program instructions received from a program source, such as software or firmware, and the ultrasound imaging data received from ultrasound imaging probe 18 and/or previously stored in non-transitory electronic memory 22-2 to which imaging control circuit 22 has electronic access, so as to generate an ultrasound image 60 (see FIG. 2) for display on display screen 24. Stated differently, imaging control circuit 22 generates ultrasound image 60 for display on display screen 24 from ultrasound imaging data collected from ultrasound imaging space 30, with the ultrasound imaging data having been generated by ultrasound transducer array 18-2 of ultrasound imaging probe 18 and stored in non-transitory electronic memory 22-2.

Display screen 24 may be, or form part of, a graphical user interface, wherein display screen 24 is a touch-screen that accommodates user inputs, as well as displaying an ultrasound image formed from the 2D ultrasound slice data provided by ultrasound imaging probe 18 within the 3D imaging volume of ultrasound imaging space 30. Display screen 24 may be configured as a standard 2D display, or optionally, may be configured as a 3D display. For example, the 3D dataset captured by ultrasound imaging system 12 may be presented to the user via an autostereoscopic or other display method that presents a 3D image to the user. As such, display screen 24 may display ultrasound image 60 as a 2D or 3D ultrasound image.

Ultrasonic vibration system 14 includes an ultrasonic generator 32, an ultrasonic transducer 34, and a medical ultrasonic object 36. In the present example, medical ultrasonic object 36 is a vibrating device, such as a portion of an ultrasonic catheter.

Ultrasonic generator 32 is operatively coupled to medical ultrasonic object 36 via ultrasonic transducer 34. More particularly, ultrasonic generator 32 is communicatively coupled to ultrasonic transducer 34 via a communication cable 38, such as a multi-wire cable. Ultrasonic generator 32 is configured to generate electrical signals at ultrasonic frequencies, which in turn are supplied to ultrasonic transducer 34 via communication cable 38. Ultrasonic transducer 34, such as an acoustical horn, converts the ultrasonic electrical signals received from ultrasonic generator 32 into mechanical vibration waves. Ultrasonic transducer 34 is mechanically and/or acoustically coupled to medical ultrasonic object 36, so as to transfer the ultrasonic vibrational waves to medical ultrasonic object 36.

Ultrasonic generator 32 includes a generator control circuit 40. Generator control circuit 40 is an electrical circuit that has data processing capability and command generating capability. In the present embodiment, generator control circuit 40 has a microprocessor 40-1 and associated non-transitory electronic memory 40-2, as well as input/output (I/O) circuitry. Microprocessor 40-1 and associated non-transitory electronic memory 40-2 are commercially available components, as will be recognized by one skilled in the art. Microprocessor 40-1 may be in the form of a single microprocessor, or two or more parallel microprocessors, as is known in the art. Non-transitory electronic memory 40-2 may include multiple types of digital data memory, such as random access memory (RAM), non-volatile RAM (NVRAM), read only memory (ROM), and/or electrically erasable programmable read-only memory (EEPROM). Non-transitory electronic memory 40-2 may further include mass data storage in one or more of the electronic memory forms described above, or on a computer hard drive or optical disk. Alternatively, generator control circuit 40 may be assembled as one or more Application Specific Integrated Circuits (ASIC).

Generator control circuit 40 is communicatively coupled to imaging control circuit 22 via a communication link 42, such as a wired cable, or alternatively by a wireless interface operating with a short range wireless protocol, such as Bluetooth®.

Generator control circuit 40 is configured to operate ultrasonic generator 32 to generate a variable ultrasonic electrical signal, wherein the operational frequency of the ultrasonic signal alternatingly switches between an ultrasonic work frequency and a tracking frequency that is different from the ultrasonic work frequency. More particularly, generator control circuit 40 processes program instructions received from a program source, such as software or firmware, to which generator control circuit 40 has electronic access, so as to operate ultrasonic generator 32 to generate the variable ultrasonic electrical signal at multiple ultrasonic operational frequencies, i.e., at least one ultrasonic work frequency and a tracking frequency that is different from the ultrasonic work frequency. Generator control circuit 40 also executes program instructions to send a notification, e.g., a toggle bit, or message packet, via a communication link 42 to imaging control circuit 22 when generator control circuit 40 has switched the operational frequency of the ultrasonic electrical signal generated by ultrasonic generator 32 from the ultrasonic work frequency to the tracking frequency.

In the present exemplary embodiment, the ultrasonic work frequency may be an operational frequency in a frequency range of, for example, about 20 kilohertz (kHz) to about 40 kHz, and the tracking frequency is a different operational frequency that effects a vibrational velocity of medical ultrasonic object 36, e.g., a distal tip of an elongate ultrasonic corewire, in a range of about one centimeter per second to about 500 centimeters per second. In some implementations, it may be desirable for the tracking frequency to be lower than the ultrasonic work frequency, and in other implementations, it may be desirable for the tracking frequency to be higher than the ultrasonic work frequency.

As used herein, the term "about" means the indicated amount in the indicated unit, plus or minus 10 percent.

Each of the operational frequencies, i.e., the ultrasonic work frequency and the tracking frequency, are alternatingly generated by ultrasonic generator 32, and in turn coupled to medical ultrasonic object 36 via ultrasonic transducer 34. In the present embodiment, medical ultrasonic object 36 may be a vibrating portion of an ultrasonic catheter 44.

For example, referring to FIGS. 1 and 2, ultrasonic catheter 44 has a catheter sheath 46 and a corewire 48. Catheter sheath 46 has a proximal end 46-1, a distal end 46-2, and a lumen 46-3 extending between proximal end 46-1 and distal end 46-2 in a longitudinal direction. Corewire 48 is movably disposed within lumen 46-3 of catheter sheath 46. Corewire 48 may be formed as a unitary elongate member made of a flexible metal, such as nitinol, to serve as an ultrasound transmission member.

Corewire 48 has a proximal portion 48-1, a distal portion 48-2, and a distal tip 48-3. Proximal portion 48-1 of corewire 48 is mechanically and/or acoustically coupled to ultrasonic generator 32 via ultrasonic transducer 34, such that ultrasonic transducer 34 transfers vibration motion to corewire 48, and more particularly, to distal portion 48-2 of corewire 48. Distal portion 48-2 of corewire 48 may be exposed from distal end 46-2 of catheter sheath 46, such as for example, in the range of 5 millimeters (mm) to 200 mm, with the exposed distal portion 48-2 of corewire 48 being referred to herein as an active section having distal tip 48-3.

Referring to FIG. 2, there is shown a graphical representation of a portion of a patient 50, e.g., a portion of a leg, having tissue 52 through which a blood vessel 54 extends. Located in blood vessel 54 is a calcified occlusion 56. Ultrasonic catheter 44 is inserted into blood vessel 54 via an introducer cannula 58. During an occlusion clearing procedure, distal portion 48-2 of corewire 48 is brought into engagement with calcified occlusion 56. Distal portion 48-2 of corewire 48 is excited at the ultrasonic work frequency by the ultrasound wave generated by ultrasonic transducer 34, which in turn generates longitudinal and transverse mechanical vibration at distal portion 48-2 of corewire 48. This longitudinal and transverse mechanical vibration at distal portion 48-2, including distal tip 48-3, of corewire 48 ablates calcified occlusion 56 in blood vessel 54 of patient 50.

In order to locate and track the location of medical ultrasonic object 36, e.g., distal tip 48-3, of corewire 48, generator control circuit 40 alternatingly switches between the ultrasonic work frequency and the tracking frequency, with the tracking frequency being different from the ultrasonic work frequency. Generator control circuit 40 executes program instructions to send a notification, e.g., a toggle bit, or message packet, to imaging control circuit 22 of ultrasound imaging system 12 when generator control circuit 40 switches the operational frequency of the ultrasonic electrical signal generated by ultrasonic generator 32 from the ultrasonic work frequency to the tracking frequency. Imaging control circuit 22 of ultrasound imaging system 12 is configured to respond to the notification by executing program instructions to initiate a search in the ultrasound imaging space 30, i.e., the associated 3D imaging data, to locate distal tip 48-3 of the corewire 48 of ultrasonic catheter 44 that is vibrating at the tracking frequency, and once located, to indicate a location of distal tip 48-3 in an ultrasound image 60 displayed on display screen 24. The act of indicating the location of distal tip 48-3 in ultrasound image 60 displayed on display screen 24 may be achieved by imaging control circuit 22 executing program instructions to highlight a portion, represented by diamond 62, of ultrasound image 60 displayed on display screen 24 that corresponds to distal tip 48-3 of corewire 48 of ultrasonic catheter 44. As used herein, to "highlight" means to provide a contrasting color or brightness relative to the brightness and/or color of ultrasound image 60.

Generator control circuit 40 may alternatingly switch between the ultrasonic work frequency and a tracking frequency on a periodic basis, e.g., as in a continuous loop, wherein a time ratio of the ultrasonic work frequency to the tracking frequency may be in a range of 80:20 to 95:5. For example, the duration of the ultrasonic work frequency may be at least four times longer than the duration of the tracking frequency, so that the duration of the tracking frequency does not adversely impact the occlusion clearing performance of distal tip 48-3 of corewire 48. Also, the switching between the ultrasonic work frequency and the tracking frequency may occur at a switching frequency of about one Hz to about 1000 Hz. At the end of the tracking frequency duration, generator control circuit 40 executes program instructions to switch back to the ultrasonic work frequency. Further, generator control circuit 40 may execute program instructions as a continuous loop to repeat each of the acts of switching to the tracking frequency, sending the notification, and switching back to the ultrasonic work frequency at a set or variable repetition frequency, wherein the repetition frequency may be in a range of about one Hz to about 1000 Hz.

Figure 3:
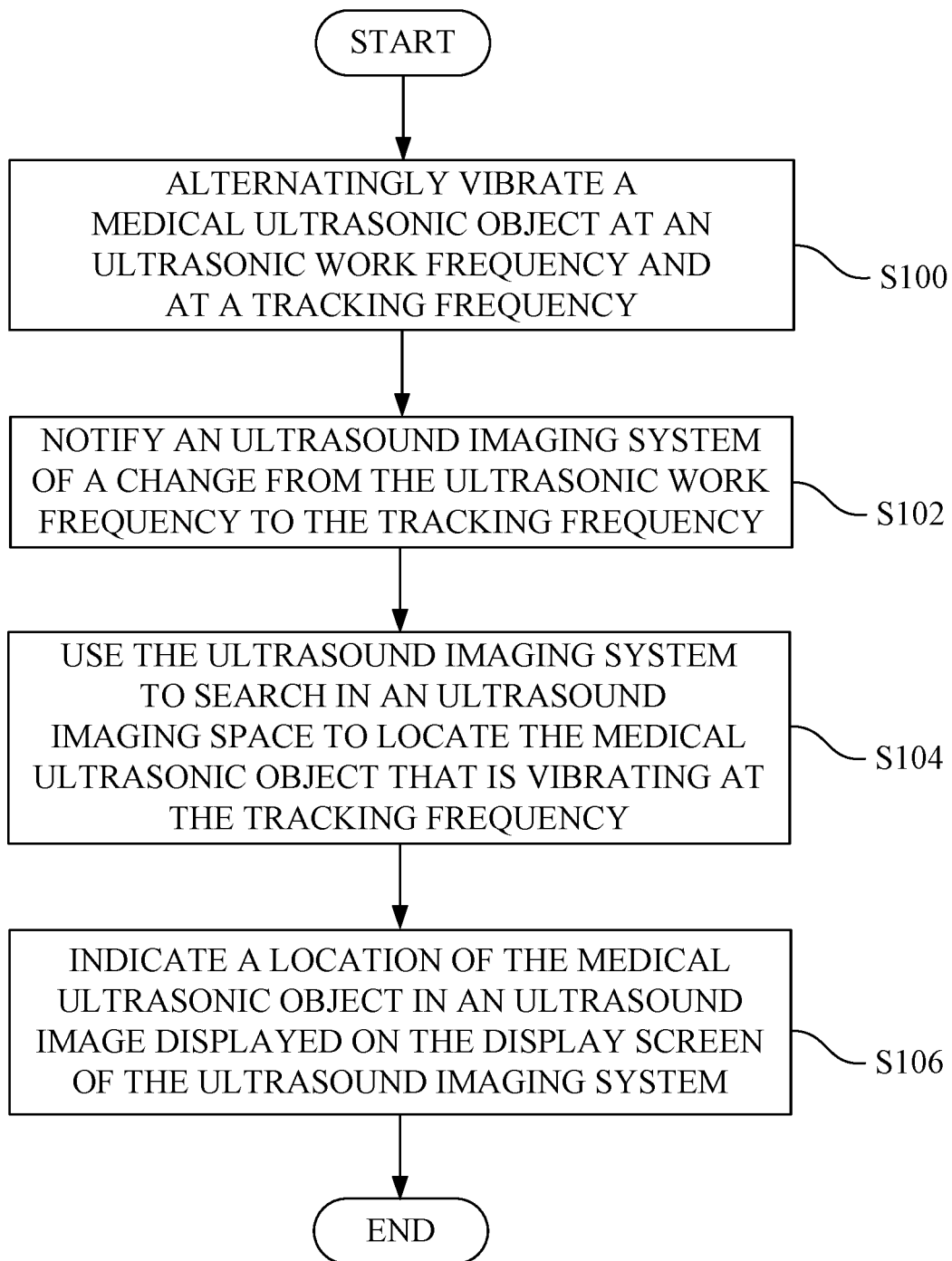
FIG. 3 is a flowchart of a method for locating and/or tracking a medical ultrasonic object using the vascular occlusion treatment system of FIG. 1.

Referring to FIG. 3, there is shown a flowchart of a method for locating and/or tracking medical ultrasonic object 36 using ultrasound imaging system 12 having ultrasound imaging probe 18 and display screen 24. As more fully described above, ultrasound imaging probe 18 generates ultrasound imaging data in ultrasound imaging space 30 for generation of ultrasound image 60 for display on display screen 24.

At step S100, medical ultrasonic object 36 is alternatingly vibrated at an ultrasonic work frequency and at a tracking frequency, with the ultrasonic work frequency and the tracking frequency being different frequencies. Each of the ultrasonic work frequency and the tracking frequency are predetermined, and may be established for reference in non-transitory electronic memory 40-2 of generator control circuit 40. Medical ultrasonic object 36 may be, for example, distal tip 48-3 of corewire 48 carried by ultrasonic catheter 44, or distal portion 48-2 including distal tip 48-3 of corewire 48. For example, in step S100, an operation of ultrasonic catheter 44 is alternated between vibrating distal tip 48-3 at the ultrasonic work frequency and vibrating distal tip 48-3 at the tracking frequency.

The ultrasonic work frequency may be an operational frequency generated by ultrasonic generator 32 in a range of about 20 kHz to about 40 kHz, and the tracking frequency may be an operational frequency generated by ultrasonic generator 32 that effects a vibrational velocity of medical ultrasonic object 36 in a range of about one centimeter per second to about 500 centimeters per second. The tracking frequency may be higher than the ultrasonic work frequency, or alternatively, the tracking frequency may be lower than the ultrasonic work frequency.

A time ratio of the ultrasonic work frequency to the tracking frequency is in a range of 80:20 to 95:5, wherein following a predetermined duration of the tracking frequency, the operational frequency of ultrasonic generator 32 is switched back to the ultrasonic work frequency. Following a predetermined duration of the tracking frequency, the method switches back to the ultrasonic work frequency. The act of alternatingly vibrating at step S100 alternatingly switches between the ultrasonic work frequency and the tracking frequency at a switching frequency of about one Hz to about 1000 Hz.

At step S102, ultrasound imaging system 12 is notified of a change from the ultrasonic work frequency to the tracking frequency. In particular, generator control circuit 40 executes program instructions to send a notification, e.g., a toggle bit, or message packet, to imaging control circuit 22 of ultrasound imaging system 12 when generator control circuit 40 switches the operational frequency of the ultrasonic electrical signal generated by ultrasonic generator 32 from the ultrasonic work frequency to the tracking frequency.

At step S104, in response to the notification at step S102, ultrasound imaging system 12 initiates a search in ultrasound imaging space 30 using imaging data generated and collected by ultrasound imaging probe 18 to locate medical ultrasonic object 36 that is vibrating at the tracking frequency.

For example, assume medical ultrasonic object 36 is distal portion 48-2 having distal tip 48-3 of corewire 48 of ultrasonic catheter 44. In response to the notifying, a search is initiated by ultrasound imaging system 12 to locate in the ultrasound imaging space 30 the distal tip 48-3 of corewire 48 of ultrasonic catheter 44 that is vibrating at the tracking frequency. For example, assume that the tracking frequency is selected to effect a vibrational velocity of medical ultrasonic object 36 (e.g., distal tip 48-3) at about 50 centimeters per second. In such a case, for example, imaging control circuit 22 may invoke a Doppler function to search the imaging dataset associated with ultrasound imaging space 30 to identify an object that is vibrating at a velocity of about, or alternatively exactly, 50 centimeters per second so as to determine the location within ultrasound imaging space 30 of the vibrational occurrence at the vibrational velocity associated with the tracking frequency.

As a further refinement of the search, in some implementations, ultrasound imaging system 12 may consider the shape of medical ultrasonic object 36 in conjunction with locating an object vibrating at the tracking frequency.

At step S106, a location of medical ultrasonic object 36 is indicated in ultrasound image 60 displayed on display screen 24. Ultrasound image 60 may be, for example, a 2D ultrasound image or 3D ultrasound image. Referring again to FIG. 2, the act of indicating the location of distal tip 48-3 in ultrasound image 60 displayed on display screen 24 may be achieved by imaging control circuit 22 executing program instructions to highlight a portion, represented by diamond 62, of ultrasound image 60 displayed on display screen 24 that corresponds to medical ultrasonic object 36, e.g., distal tip 48-3 of corewire 48 of ultrasonic catheter 44.

If the medical ultrasonic object 36, e.g., distal tip 48-3 of corewire 48 of ultrasonic catheter 44, is not positioned within ultrasound imaging space 30 of ultrasound imaging probe 18, then ultrasound image 60 displayed on display screen 24 will not be able to indicate the present location of medical ultrasonic object 36. To remedy this situation, the user will move ultrasound imaging probe 18 relative to patient 50 until medical ultrasonic object 36 is positioned within ultrasound imaging space 30 of ultrasound imaging probe 18. Once medical ultrasonic object 36 is positioned within ultrasound imaging space 30, then the present location of medical ultrasonic object 36 relative to patient 50 will be indicated in ultrasound image 60 displayed on display screen 24.

Once the location of medical ultrasonic object 36 is identified, then the location of medical ultrasonic object 36 may be tracked by observation of the movement of the highlighted portion, represented by diamond 62, of ultrasound image 60 displayed on display screen 24 that corresponds to medical ultrasonic object 36.

As an alternative to the method and apparatus described above, generator control circuit 40 of ultrasonic generator 32 may be configured to alternatingly switch between an output power level for treatment and an output power level for image tracking, while using the same ultrasonic frequency. The generator output power level for treatment can transmit strong vibration energy into ultrasonic catheter 44 and cause distal portion 48-2, i.e., the active section, of corewire 48 to vibrate strongly at the ultrasonic frequency. The generator output power level for image tracking can transmit a relatively small energy into ultrasonic catheter 44 and cause distal portion 48-2, i.e., the active section, of corewire 48 to vibrate, but not have any therapeutic effect. Generator control circuit 40 is communicatively coupled to imaging control circuit 22. Generator control circuit 40 is configured to execute program instructions to send a notification to imaging control circuit 22 when generator control circuit 40 has switched from the treatment power level to the image tracking power level. Imaging control circuit 22 is configured to respond to the notification by executing program instructions to initiate a search in the ultrasound imaging space 30 utilizing a Doppler function. The Doppler function will only detect any moving components in the ultrasound imaging space 30. Therefore, the vibration of the distal portion 48-2, i.e., the active section, of corewire 48 of ultrasonic catheter 44 will be able to be detected by ultrasound imaging system 12. After active averaging and filtering, the location of the distal tip 48-3 of corewire 48 will be displayed, e.g., by highlighting represented by diamond 62, in the ultrasound image displayed on display screen 24 of ultrasound imaging system 12.

The following items also relate to the invention:

In one form, the invention relates to a vascular occlusion treatment system that includes an ultrasound imaging system and an ultrasonic vibration system. The ultrasound imaging system has an imaging control circuit communicatively coupled to each of an ultrasound imaging probe and a display screen. The ultrasound imaging system is configured to generate an ultrasound image for display on the display screen from ultrasound imaging data collected from an ultrasound imaging space. The ultrasonic vibration system has an ultrasonic generator operatively coupled to an ultrasonic catheter. The ultrasonic catheter has a corewire with a distal tip. The ultrasonic generator has a generator control circuit configured to alternatingly switch between an ultrasonic work frequency and a tracking frequency, wherein the ultrasonic work frequency and the tracking frequency may be different frequencies. The generator control circuit is communicatively coupled to the imaging control circuit. The generator control circuit is configured to execute program instructions to send a notification to the imaging control circuit when the generator control circuit has switched from the ultrasonic work frequency to the tracking frequency. The imaging control circuit is configured to respond to the notification by executing program instructions to: initiate a search in the ultrasound imaging space to locate the distal tip of the corewire of the ultrasonic catheter that is vibrating at the tracking frequency, and indicate a location of the distal tip in the ultrasound image displayed on the display screen.

The ultrasound imaging system may be configured to represent the ultrasound imaging space by 3D imaging data and the ultrasound image may be a 2D ultrasound image or a 3D ultrasound image. A time ratio of the ultrasonic work frequency to the tracking frequency may be about 80:20 to 95:5. Optionally, following a predetermined duration of the tracking frequency, the generator control circuit executes program instructions to switch back to the ultrasonic work frequency. The generator control circuit may execute program instructions to switch between the ultrasonic work frequency and the tracking frequency at a switching frequency of about one Hz to about 1000 Hz. More particularly, the generator control circuit may execute program instructions to repeat the acts of switching to the tracking frequency, sending the notification, and switching back to the ultrasonic work frequency at a repetition frequency of about one Hz to about 1000 Hz. The tracking frequency may effect a vibrational velocity of the distal tip of the ultrasonic catheter in a range of about one centimeter per second to about 500 centimeters per second. The tracking frequency may be higher than the ultrasonic work frequency. Alternatively, the tracking frequency may be lower than the ultrasonic work frequency. The imaging control circuit may be configured to indicate the location of the distal tip in the ultrasound image displayed on the display screen by executing program instructions to highlight a portion of the ultrasound image displayed on the display screen that corresponds to the distal tip of the corewire of the ultrasonic catheter.

In another form, the invention relates to a method, e.g., for operating medical devices, for tracking a medical ultrasonic object using an ultrasound imaging system having an ultrasound imaging probe and a display screen, the ultrasound imaging probe generating ultrasound imaging data in an ultrasound imaging space for generation of an ultrasound image for display on the display screen. The method includes alternatingly vibrating the medical ultrasonic object at an ultrasonic work frequency and at a tracking frequency, the ultrasonic work frequency and the tracking frequency being different frequencies; notifying the ultrasound imaging system of a change from the ultrasonic work frequency to the tracking frequency; initiating a search by the ultrasound imaging system to search in the ultrasound imaging space to locate the medical ultrasonic object that is vibrating at the tracking frequency; and indicating a location of the medical ultrasonic object in the ultrasound image displayed on the display screen.

The medical ultrasonic object may be a distal tip of a corewire carried by an ultrasonic catheter. The ultrasound imaging space may be represented by 3D imaging data and the ultrasound image may be a 2D ultrasound image or a 3D ultrasound image. A time ratio of the ultrasonic work frequency to the tracking frequency may be about 80:20 to 95:5. Optionally, following a predetermined duration of the tracking frequency, the method includes switching back to the ultrasonic work frequency. The act of alternatingly vibrating may include switching between the ultrasonic work frequency and the tracking frequency at a switching frequency of about one Hz to about 1000 Hz. The act of alternatingly vibrating may include repeating the acts of switching to the tracking frequency, notifying, and switching back to the ultrasonic work frequency at a repetition frequency of about one Hz to about 1000 Hz. The tracking frequency may effect a vibrational velocity of the medical ultrasonic object in a range of about one centimeter per second to about 500 centimeters per second. The tracking frequency may be higher than the ultrasonic work frequency. Alternatively, the tracking frequency may be may be lower than the ultrasonic work frequency. The act of indicating may include highlighting a portion of the ultrasound image displayed on the display screen that corresponds to the medical ultrasonic object.

In another form, the invention relates to a method, e.g., for operating medical devices, to locate a distal tip of an ultrasonic catheter used in conjunction with an ultrasound imaging system having an ultrasound imaging probe and a display screen, the ultrasound imaging probe generating ultrasound imaging data in an ultrasound imaging space for generation of an ultrasound image for display on the display screen. The method includes establishing an ultrasonic work frequency for the distal tip of the corewire of the ultrasonic catheter; establishing a tracking frequency for the distal tip of the corewire of the ultrasonic catheter that is different from the ultrasonic work frequency; alternating an operation of the ultrasonic catheter between vibrating the distal tip at the ultrasonic work frequency and vibrating the distal tip at the tracking frequency; notifying the ultrasound imaging system of the change in operation of the ultrasonic catheter from the ultrasonic work frequency to the tracking frequency; in response to the notifying, initiating a search by the ultrasound imaging system to locate in the ultrasound imaging space the distal tip of the corewire of the ultrasonic catheter that is vibrating at the tracking frequency; and indicating a location of the distal tip of the corewire of the ultrasonic catheter in the ultrasound image displayed on the display screen.

The ultrasound imaging space may be represented by 3D imaging data and the ultrasound image may be a 2D ultrasound image or a 3D ultrasound image. A time ratio of the ultrasonic work frequency to the tracking frequency is optionally in a range of 80:20 to 95:5. Optionally, following a predetermined duration of the tracking frequency, the method includes switching back to the ultrasonic work frequency. The act of alternating an operation of the ultrasonic catheter may include switching from the ultrasonic work frequency to the tracking frequency at a switching frequency of about one Hz to about 1000 Hz.

The act of alternating an operation of the ultrasonic catheter may include repeating the acts of switching to the tracking frequency, notifying, and switching back to the ultrasonic work frequency at a repetition frequency of about one Hz to about 1000 Hz. The tracking frequency may effect a vibrational velocity of the distal tip of the ultrasonic catheter in a range of about one centimeter per second to about 500 centimeters per second. The tracking frequency may be higher than the ultrasonic work frequency. Alternatively, the tracking frequency may be lower than the ultrasonic work frequency. The act of indicating may include highlighting a portion of the ultrasound image displayed on the display screen that corresponds to the distal tip of the corewire of the ultrasonic catheter.

In another form, the invention relates to an alternative vascular occlusion treatment system. The system includes an ultrasound imaging system and an ultrasonic vibration system. The ultrasound imaging system has an imaging control circuit communicatively coupled to each of an ultrasound imaging probe and a display screen. The ultrasound imaging system is configured to generate an ultrasound image for display on the display screen from ultrasound imaging data collected from an ultrasound imaging space. The ultrasonic vibration system has an ultrasonic generator operatively coupled to an ultrasonic catheter. The ultrasonic catheter has a corewire with a distal portion having a distal tip. The ultrasonic generator has a generator control circuit configured to alternatingly switch between an output power level for treatment and an output power level for image tracking, while maintaining the same ultrasonic frequency. The generator control circuit is communicatively coupled to the imaging control circuit. The generator control circuit is configured to execute program instructions to send a notification to the imaging control circuit when the generator control circuit has switched from the treatment power level to the image tracking power level. The imaging control circuit is configured to respond to the notification by executing program instructions to: initiate a search in the ultrasound imaging space utilizing a Doppler function to detect any moving components in the ultrasound imaging space; and indicate a location of the distal tip in the ultrasound image displayed on the display screen.

The ultrasound imaging system may be configured to represent ultrasound imaging space by 3D imaging data and the ultrasound image may be a 2D ultrasound image or a 3D ultrasound image. The imaging control circuit may be configured to indicate the location of the distal tip in the ultrasound image displayed on the display screen by executing program instructions to highlight a portion of the ultrasound image displayed on the display screen that corresponds to the distal tip of the corewire of the ultrasonic catheter.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A vascular occlusion treatment system, comprising:
an ultrasound imaging system having an imaging control circuit communicatively coupled to each of an ultrasound imaging probe and a display screen, the ultrasound imaging system configured to generate an ultrasound image for display on the display screen from ultrasound imaging data collected from an ultrasound imaging space; and
an ultrasonic vibration system having an ultrasonic generator operatively coupled to an ultrasonic catheter, the ultrasonic catheter having a corewire with a distal tip, the ultrasonic generator having a generator control circuit configured to alternatingly switch between an ultrasonic work frequency and a tracking frequency, the generator control circuit being communicatively coupled to the imaging control circuit,
the generator control circuit configured to execute program instructions to send a notification to the imaging control circuit when the generator control circuit has switched from the ultrasonic work frequency to the tracking frequency;
the imaging control circuit configured to respond to the notification by executing program instructions to:
initiate a search for the tracking frequency in the ultrasound imaging space to locate the distal tip of the corewire of the ultrasonic catheter that is vibrating at the tracking frequency; and
indicate a location of the distal tip in the ultrasound image displayed on the display screen.

2. The vascular occlusion treatment system of claim 1, wherein the ultrasound imaging space is represented by 3D imaging data and the ultrasound image is a 2D ultrasound image or a 3D ultrasound image.

3. The vascular occlusion treatment system of claim 1, wherein a time ratio of the ultrasonic work frequency to the tracking frequency is in a range of 80:20 to 95:5.

4. The vascular occlusion treatment system of claim 1, wherein following a predetermined duration of the tracking frequency, the generator control circuit executes program instructions to switch back to the ultrasonic work frequency.

5. The vascular occlusion treatment system of claim 1, wherein the generator control circuit executes program instructions to switch between the ultrasonic work frequency and the tracking frequency at a switching frequency of about one Hz to about 1000 Hz.

6. The vascular occlusion treatment system of claim 1, wherein the generator control circuit executes program instructions to repeat the acts of switching to the tracking frequency, sending the notification, and switching back to the ultrasonic work frequency at a repetition frequency of about one Hz to about 1000 Hz.

7. The vascular occlusion treatment system of claim 1, wherein the tracking frequency effects a vibrational velocity of the distal tip of the ultrasonic catheter in a range of about one centimeter per second to about 500 centimeters per second.

8. The vascular occlusion treatment system of claim 1, wherein the tracking frequency is higher than the ultrasonic work frequency.

9. The vascular occlusion treatment system of claim 1, wherein the tracking frequency is lower than the ultrasonic work frequency.

10. The vascular occlusion treatment system of claim 1, wherein to indicate the location of the distal tip in the ultrasound image displayed on the display screen comprises the imaging control circuit executing program instructions to highlight a portion of the ultrasound image displayed on the display screen that corresponds to the distal tip of the corewire of the ultrasonic catheter.

11. A method for tracking a medical ultrasonic object using an ultrasound imaging system having an ultrasound imaging probe and a display screen, the ultrasound imaging probe generating ultrasound imaging data in an ultrasound imaging space for generation of an ultrasound image for display on the display screen, comprising:
alternatingly vibrating, with a generator control circuit, the medical ultrasonic object at an ultrasonic work frequency and at a tracking frequency, the ultrasonic work frequency and the tracking frequency being different frequencies;
notifying, with the generator control circuit, the ultrasound imaging system of a change from the ultrasonic work frequency to the tracking frequency;
initiating a search by the ultrasound imaging system to search for the tracking frequency in the ultrasound imaging space to locate the medical ultrasonic object that is vibrating at the tracking frequency; and
indicating a location of the medical ultrasonic object in the ultrasound image displayed on the display screen.

12. The method of claim 11, wherein the medical ultrasonic object is a distal tip of a corewire carried by an ultrasonic catheter.

13. The method of claim 11, wherein the ultrasound imaging space is represented by 3D imaging data and the ultrasound image is a 2D ultrasound image or a 3D ultrasound image.

14. The method of claim 11, wherein a time ratio of the ultrasonic work frequency to the tracking frequency is in a range of 80:20 to 95:5.

15. The method of claim 11, wherein following a predetermined duration of the tracking frequency, the method comprising switching back to the ultrasonic work frequency.

16. The method of claim 11, wherein the act of alternatingly vibrating comprises switching between the ultrasonic work frequency and the tracking frequency at a switching frequency of about one Hz to about 1000 Hz.

17. The method of claim 11, wherein the act of alternatingly vibrating comprises repeating the acts of switching to the tracking frequency, notifying, and switching back to the ultrasonic work frequency at a repetition frequency of about one Hz to about 1000 Hz.

18. The method of claim 11, wherein the tracking frequency effects a vibrational velocity of the medical ultrasonic object in a range of about one centimeter per second to about 500 centimeters per second.

19. The method of claim 11, wherein the tracking frequency is higher than the ultrasonic work frequency.

20. A vascular occlusion treatment system, comprising:
an ultrasound imaging system having an imaging control circuit communicatively coupled to each of an ultrasound imaging probe and a display screen, the ultrasound imaging system configured to generate an ultrasound image for display on the display screen from ultrasound imaging data collected from an ultrasound imaging space; and an ultrasonic vibration system having an ultrasonic generator operatively coupled to an ultrasonic catheter, ultrasonic catheter having a corewire with a distal portion having a distal tip, the ultrasonic generator having a generator control circuit configured to alternatingly switch between an output power level for treatment and an output power level for image tracking, while maintaining the same ultrasonic frequency, the generator control circuit being communicatively coupled to the imaging control circuit, the generator control circuit configured to execute program instructions to send a notification to the imaging control circuit when the generator control circuit has switched from the treatment power level to the image tracking power level, the imaging control circuit configured to respond to the notification by executing program instructions to:

initiate a search in the ultrasound imaging space utilizing a Doppler function to detect any moving components in the ultrasound imaging space; and indicate a location of the distal tip in the ultrasound image displayed on the display screen.

* * * * *